United States Patent
Yamada et al.

[19]

[11] Patent Number: 5,807,337
[45] Date of Patent: Sep. 15, 1998

[54] LIQUID INFUSION APPARATUS

[75] Inventors: Keiichi Yamada; Junichi Yamanaka, both of Osaka, Japan

[73] Assignee: Daiken Iki Co., Ltd., Osaka, Japan

[21] Appl. No.: 564,151

[22] PCT Filed: Apr. 24, 1995

[86] PCT No.: PCT/JP95/00831

§ 371 Date: Dec. 21, 1995

§ 102(e) Date: Dec. 21, 1995

[87] PCT Pub. No.: WO95/28977

PCT Pub. Date: Nov. 2, 1995

[30]     Foreign Application Priority Data

Apr. 27, 1994 [JP]   Japan ........................... 6-90317

[51] Int. Cl.⁶ ................................................ A61M 37/00
[52] U.S. Cl. ........................................... 604/143; 604/131
[58] Field of Search ......................... 604/131, 141–149, 604/191; 222/389

[56]              References Cited

U.S. PATENT DOCUMENTS

| | | | |
|---|---|---|---|
| 3,863,624 | 2/1975 | Gram ................................. | 604/191 X |
| 4,036,232 | 7/1977 | Genese ................................ | 604/143 |
| 4,180,067 | 12/1979 | Derlien ............................... | 604/143 X |
| 4,505,701 | 3/1985 | Navato . | |
| 4,561,856 | 12/1985 | Cochran . | |
| 4,666,430 | 5/1987 | Brown et al. ....................... | 604/141 |
| 4,676,256 | 6/1987 | Golden .............................. | 604/148 X |
| 4,765,509 | 8/1988 | Eisenhut et al. .................... | 222/389 X |
| 4,773,900 | 9/1988 | Cochran ............................. | 604/143 |
| 4,813,937 | 3/1989 | Vaillancourt ........................ | 604/131 |
| 4,997,420 | 3/1991 | LeFevre . | |
| 5,024,664 | 6/1991 | Mitchell ............................. | 604/143 |
| 5,059,174 | 10/1991 | Vaillancourt . | |
| 5,062,834 | 11/1991 | Gross et al. . | |
| 5,098,385 | 3/1992 | Walsh ................................. | 604/131 |
| 5,135,500 | 8/1992 | Zdeb .................................. | 604/143 |
| 5,290,259 | 3/1994 | Fischer ............................... | 604/191 X |
| 5,360,411 | 11/1994 | Mimura et al. . | |
| 5,411,485 | 5/1995 | Tennican et al. .................... | 604/191 |
| 5,454,792 | 10/1995 | Tennican et al. .................... | 604/191 |
| 5,599,315 | 2/1997 | McPhee . | |

FOREIGN PATENT DOCUMENTS

WO 92/01484   2/1992   WIPO .

*Primary Examiner*—Sam Rimell
*Assistant Examiner*—Robert V. Racunas
*Attorney, Agent, or Firm*—Sixbey, Friedman, Leedom & Ferguson; David S. Safran

[57]            ABSTRACT

The present invention relates particularly to a liquid infusion apparatus useful for infusing a medicinal liquid into a human or animal body. A liquid infusion apparatus 10 according to the present invention includes: a casing (13) having a load chamber (12) to be loaded with a liquid; a movable member (14) forming part of a wall of the load chamber (12) and adapted to reciprocate with respect to the casing (13) to vary the volume of the load chamber (12); a cylinder (21) integrally coupled to the casing (13) or the movable member (14); a piston (22) axially slidably and airtightly fitted in the cylinder (21); the casing (13) being formed with an injection port (15) and a spouting port (16) which communicate with the load chamber; the cylinder (21) and the piston (22) defining an airtight cylinder chamber (23) in a vacuum condition when the piston (22) is moved in the direction away from the cylinder (21); and the movable member (14) and the piston (22) being cooperatively interconnected through a cooperative means (25) so as to decrease the volume of the load chamber (12) in proportion to a decrease in the volume of the cylinder chamber (23).

16 Claims, 13 Drawing Sheets

LIQUID INFUSION APPARATUS

TECHNICAL FIELD

The present invention relates to apparatus for infusing a liquid into a subject for infusion at a constant pressure and, more particularly, to apparatus for infusing a medicinal liquid into a human or animal body.

BACKGROUND ART

In infusing into the body of a patient a medicinal liquid such as a transfusion liquid (nutritive agent), an anticoagulant and a carcinostatic agent, a constant quantity of the medicinal liquid is sometimes desired to be infused over a long time.

To infuse a medicinal liquid continuously at a constant flow rate, there are conventionally used an electrically-driven syringe pump and a balloon infuser.

The electrically-driven syringe pump in general is heavy and hence is impossible to be moved as a patient moves. In addition, it is complicated in structure and expensive.

The balloon infuser is adapted to infuse a medicinal liquid by utilizing a contraction force of a balloon expanded by the medicinal liquid loaded therein to spout the medicinal liquid. Such an arrangement does not necessarily ensure a constant spouting pressure from the beginning to end of the contraction of the balloon. In addition, balloons usable for the balloon infuser are expensive. For these reasons the balloon infuser is also costly though is lighter than the electrically-driven syringe pump.

It is, therefore, an object of the present invention to provide a liquid infusion apparatus which is simple in structure and hence can be easily manufactured at reduced cost, while ensuring a constant spouting pressure regardless of the quantity of a liquid to be spouted.

DISCLOSURE OF THE INVENTION

To attain the foregoing object, the following technical means are taken in the present invention.

That is, according to the present invention there is provided a liquid infusion apparatus comprising: a casing having a load chamber to be loaded with a liquid; a movable member forming part of a wall of the load chamber and adapted to reciprocate with respect to the casing to vary the volume of the load chamber; a cylinder integrally coupled to the casing or the movable member; a piston axially slidably and airtightly fitted in the cylinder; the casing being formed with an injection port and a spouting port which communicate with the load chamber; the cylinder and the piston defining an airtight cylinder chamber in a vacuum condition when the piston is moved in the direction away from the cylinder; and the movable member and the piston being cooperatively interconnected through a cooperative means so as to decrease the volume of the load chamber in proportion to a decrease in the volume of the cylinder chamber.

In the liquid infusion apparatus, the movable member may be slidably and liquid-tightly fitted in the casing; the load chamber may be a space closed by the movable member and the casing; and the casing may be transparent or translucent. Such an arrangement allows the amount of the liquid remaining in the load chamber to be readily measured by visual observation.

According to the present invention, there is also provided a liquid infusion apparatus comprising: a flexible container defining therein a load chamber to be loaded with a liquid, the flexible container being expansible and retractable so as to vary the volume of the load chamber; a casing provided at one end of the flexible container in the direction of expansion-retraction of the flexible chamber; a movable member provided at the other end of the flexible chamber and adapted to reciprocate with respect to the casing so as to vary the volume of the load chamber; a cylinder integrally coupled to the casing or the movable member; a piston axially slidably and airtightly fitted in the cylinder; the flexible container being formed with an injection port and a spouting port which communicate with the load chamber; the cylinder and the piston defining an airtight cylinder chamber in a vacuum condition when the piston is moved in the direction away from the cylinder; and the movable member and the piston being cooperatively interconnected through a cooperative means so as to decrease the volume of the load chamber in proportion to a decrease in the volume of the cylinder chamber.

In the apparatus of the present invention, only one port may be provided to serve as both the injection port and the spouting port.

Alternatively, the injection port and the spouting port may be provided separately, and the injection port may be provided with a valve device (for example, one-way valve or closing valve) for preventing, as required, the liquid in the load chamber from flowing out of the injection port, so as to achieve continuous use by supplementing liquid to the load chamber during the spouting of the liquid therefrom. It should be noted that the spouting port may be provided with a closing valve or a flow rate control valve.

Further, to make the pressure of the liquid spouting from the load chamber adjustable, plural pairs of cylinder and piston may be provided, at least one of the cylinders defining a communicating port through which the cylinder chamber communicates with the atmosphere and which is closable by way of an open-close means.

An arrangement may be adopted such that the casing and the cylinder are coupled parallel to each other through a coupling member, that the cooperative means comprises a first plunger projecting axially outwardly from an open end of the casing and a second plunger projecting axially outwardly from an open end of the cylinder, and that an engagement-disengagement means is provided for disengageably interconnecting the first and second plungers.

As a liquid infusion apparatus of a vertical type wherein the casing and the cylinder are coaxially serially interconnected, the following arrangement is optimal.

In this case, according to the present invention there is provided a liquid infusion apparatus comprising: a casing shaped cylindrical and including a bottom wall portion which is formed with a liquid injection port and is closing one end of the casing with the other end opened, and a peripheral wall defining a small hole for communication between the inside of the casing and the atmosphere; a movable member liquid-tightly and axially movably inserted into the casing so as to define within the casing and adjacent the one end thereof a load chamber for storing a liquid from the injection port; a piston coaxially and cooperatively connected to the movable member through a connection rod extending toward the other end of the casing; a cylinder having one end closed by a bottom portion into which the connection rod is airtightly inserted and the other end communicating with the atmosphere, the cylinder being airtightly and axially movably fitted around the piston; and a connection means for coaxially connecting the cylinder to the casing by screwing the one end of the cylinder into the opened other end of the casing.

In this apparatus in particular, it is recommended that the connection rod be made to have a length such that when the one end of the cylinder is screwed into the opened other end of the casing with the movable member within the casing being located closest to the one end of the casing, a vacuum cylinder chamber is already defined between the bottom portion of the cylinder and the piston within the cylinder.

If the small hole of the peripheral wall of the casing which is situated on the side where the other end of the casing exists is covered with a filter preventing penetration of bacteria into the casing, a patient is prevented from infection by bacteria through the liquid in the casing even when the infusion apparatus is continuously used.

(Operation of the Invention)

According to the liquid infusion apparatus of the present invention, the cylinder chamber is in a vacuum condition and, hence, the piston is pressed by the atmospheric pressure thereby moving relative to the cylinder so as to reduce the volume of the cylinder chamber. Whereupon, the piston cooperatively connected to the movable member also moves relative to the casing, so that the volume of the load chamber decreases to spout the liquid in the load chamber from the spouting port.

At this time, the decrease in the volume of the cylinder chamber is proportional to that in the volume of the load chamber, while the force pressing the piston by the atmospheric pressure is constant in the atmosphere. Consequently, the pressure to spout the liquid from the load chamber is constant regardless of the amount of a move of the piston and regardless of the amount of the liquid remaining in the load chamber.

If the movable member is slidably and liquid-tightly fitted into the casing and the space closed by the movable member and the casing is used as the load chamber, the amount of a move of the movable member relative to the casing is proportional to a variation in the volume of the load chamber. In addition, the casing is transparent or translucent. This arrangement enables an exact measurement of the liquid in the load chamber from the exterior.

Although a sealing structure is required in liquid-tightly fitting the movable member into the casing, the use of the flexible container defining an internal space which serves as the load chamber allows such a sealing structure to be omitted and hence provides a simplified structure.

In the liquid infusion apparatus with one injection-spouting port, the injection of the liquid into and the spouting thereof from the load chamber are effected through such an injection-spouting port.

On the other hand, in the apparatus having an injection port and a spouting port separately with the injection port being provided with a valve device, the liquid injected into the load chamber through the injection port is prevented from spouting from the injection port by the valve device. When the spouting port is opened, the spouting of the liquid at a constant pressure is initiated. When the liquid is to be supplemented, supplementary liquid should be injected into the load chamber through the injection port.

In the liquid infusion apparatus having plural pairs of cylinder and piston, when the cylinder chambers of an appropriate number of cylinders are made to communicate with the atmosphere by opening the respective communicating ports using the open-close means, the pistons inserted in such cylinders no longer receives any force to move the pistons relative to the corresponding cylinders. Hence, the pressure to spout the liquid from the load chamber is reduced accordingly.

This means that by opening the respective communicating ports of the necessary number of cylinders the spouting pressure is adjusted with ease even during the spouting of the liquid from the load chamber.

Where the engagement-disengagement means is provided for disengageably interconnecting the first plunger axially outwardly projecting from the open end of the casing and the second plunger axially outwardly projecting from the open end of the cylinder, it is possible to form the cylinder and the casing separately thereby facilitating the manufacture thereof. In addition, this makes it easy to fabricate the molds therefor, resulting in further reduced cost.

On the other hand, in the case of the liquid infusion apparatus of the vertical type wherein the casing and cylinder are coaxially and serially interconnected, the arrangement that the cylinder is connected to the opened other end of the casing using a connection means of screw-in type as above makes it possible to readily remove the casing from the cylinder after the completion of infusion of a liquid into a patient body. This allows easy cleaning or sterilization of the interior of the casing despite the fact that it is of the vertical type having the casing and the cylinder coaxially and serially interconnected.

Further, if the connection rod is made to have a length such that when the one end of the cylinder is screwed into the opened other end of the casing with the movable member within the casing being located closest to the one end of the casing, a vacuum cylinder chamber is already defined between the bottom portion of the cylinder and the piston within the cylinder, the vacuum cylinder chamber is already defined prior to the injection of a medicinal liquid into the casing. This enables the movable member to be pressed at a constant pressure due to vacuum up to the last extremity at which the volume of the load chamber assumes zero.

BEST MODE FOR CARRYING OUT THE INVENTION

Hereinafter, the embodiments of the present invention will be described with reference to the drawings.

(First Embodiment)

Figure 1:
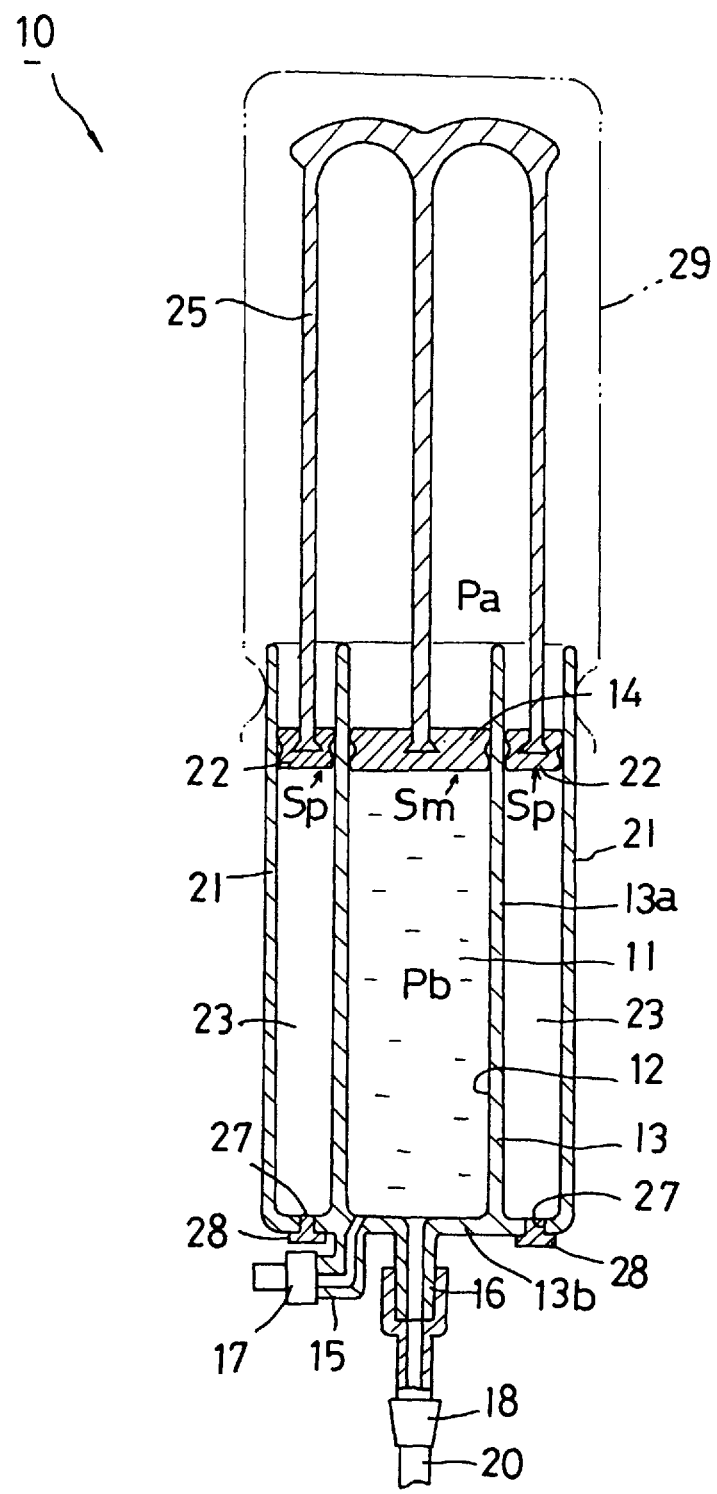
FIG. 1 is a side sectional view of a liquid infusion apparatus according to a first embodiment of the invention.
Figure 2:
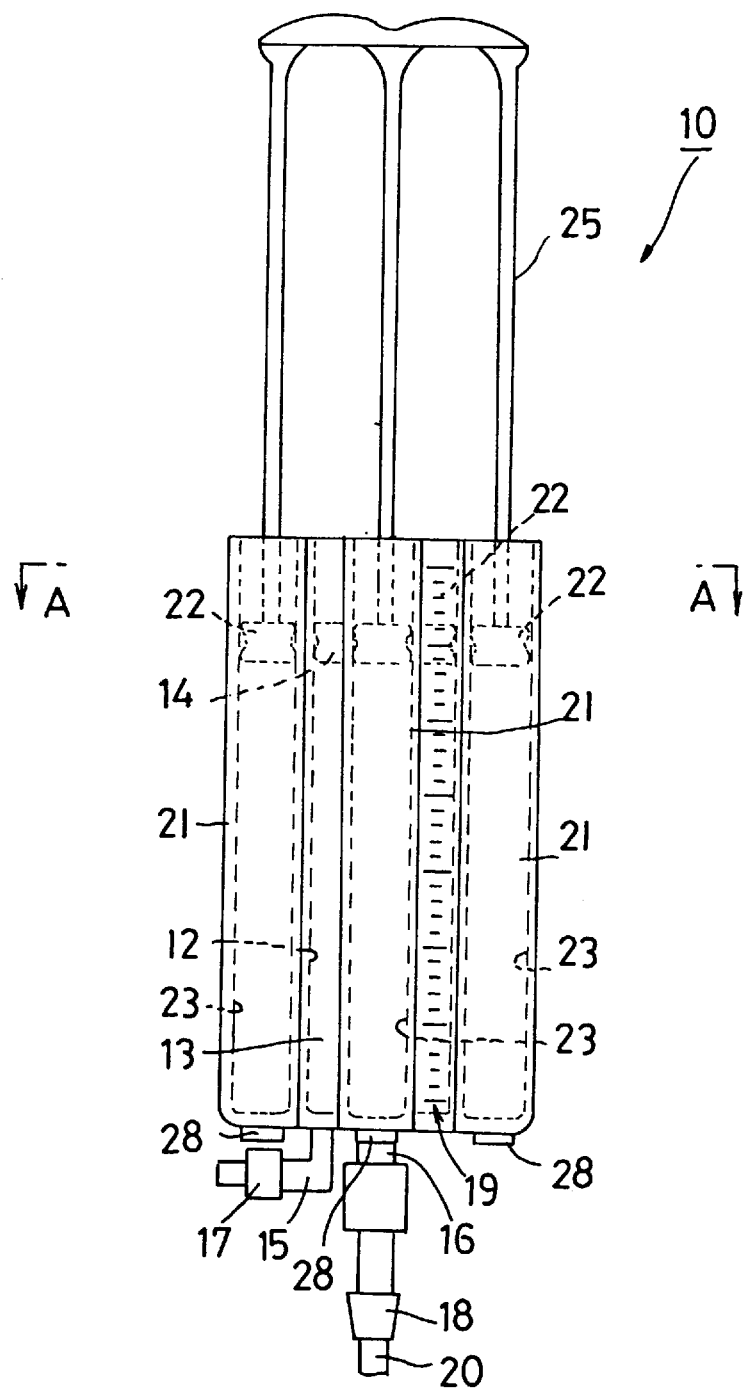
FIG. 2 is a side elevational view of the liquid infusion apparatus.
Figure 3:
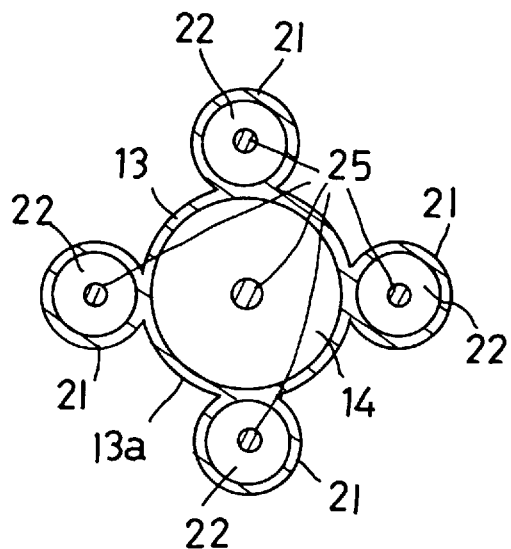
FIG. 3 is a sectional view taken along line A—A of FIG. 2.

Liquid infusion apparatus 10 according to the first embodiment shown in FIGS. 1 to 3 includes a casing 13 having a load chamber 12 to be loaded with a medicinal liquid 11. The casing 13 is formed of a transparent or translucent, easy-to-mold, rigid synthetic resin (for example, polyvinyl chloride, polypropylene, polyethylene, polycarbonate or the like) and has a cylindrical peripheral wall portion 13a and a bottom wall portion 13b closing one open end of the peripheral wall portion 13a. The peripheral wall portion 13a may be shaped prismatic.

Into the casing 13 is axially slidably and liquid-tightly fitted a movable member 14 in the form of a piston. The movable member 14 is formed of a resilient material such as rubber and is fitted into the peripheral wall portion 13a in a compressed condition, so that it closely contacts the inner periphery of the peripheral wall portion 13a of the casing 13 with no clearance therebetween.

The movable member 14 forms part of a wall of the load chamber 12, which is a space closed by the movable member 14 and the peripheral wall portion 13a and bottom wall portion 13b of the casing 13. The volume of the load chamber 12 is varied as the movable member 13 axially reciprocates with respect to the casing 13. The rear side (the reverse side of the side facing the load chamber 12) of the movable member 14 communicates with the atmosphere.

Further, the bottom wall portion 13b of the casing 13 is provided with an injection port 15 and a spouting port 16 which communicate with the load chamber 12 and are formed separately, the injection port 15 allowing a medicinal liquid to be injected into the load chamber 12 therethrough, the spouting port 16 permitting the medicinal liquid 11 in the load chamber 12 to be spouted therethrough.

To the injection port 15 is provided a valve device 17 for preventing the medicinal liquid 11 in the load chamber 12 from spouting through the injection port 15. Usable as the valve device 17 are suitable ones including an open-close valve and a one-way valve. Where the open-close valve is employed, the valve device 17 is operated to open the injection port 15 when the medicinal liquid is injected into the load chamber 12, and upon completion of the injection the valve device 17 is operated to close the injection port 15. Where the one-way valve is employed, it should be mounted so as to permit the medicinal liquid to be injected into the load chamber 12 through the injection port 15 but to prevent the medicinal liquid from spouting therethrough. Such an arrangement is more preferable in terms of convenience in handling because the valve device 17 requires no operation for injecting the medicinal liquid into the load chamber 12 through the injection port 15.

The spouting port 16 is provided with an open-close valve device 18 so as to be opened or closed by a mere single operation. To the spouting port 16 is connected a flexible tube 20 of a synthetic resin, through which the medicinal liquid spouted from the spouting port 16 is passed and then infused into a patient body.

On the outer periphery of the peripheral wall 13a of the casing 13 are provided graduations 19 at regular intervals in the axial direction. The graduations 19 may be those formed by carving cut grooves on the outer periphery of the casing 13 or by affixing a graduations printed sticker thereonto, or by other appropriate means. The graduations 19 need not necessarily be formed at regular intervals, but the graduations 19 at regular intervals can readily be read with less likelihood of being misread. Further, since the casing 13 is cylindrical in this embodiment, the position of the movable member 14 relative to the casing 13 determines the volume of the load chamber 12 exactly, thereby enabling exact measurement of the amount of the medicinal liquid 11 in the load chamber 12.

The infusion apparatus 10 of the present embodiment includes four pairs of piston 22 and cylinder 21 which serve as a driving power source for making the movable member 14 to move with respect to the casing 13 so as to decrease the volume of the load chamber 12.

Figure 4:
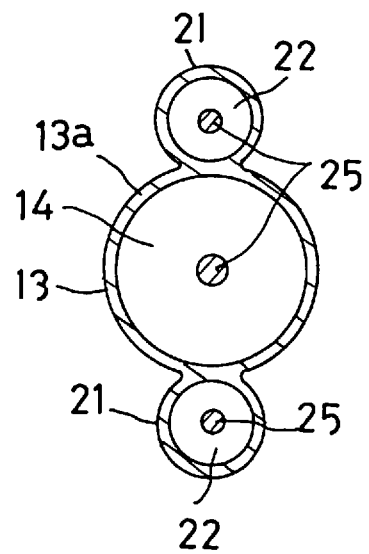
FIG. 4 is a sectional view, corresponding to FIG. 3, of a liquid infusion apparatus having two pairs of cylinder and piston.

As shown in FIG. 3, the four cylinders 21 are disposed around the cylindrical casing 13 integrally therewith. The respective axes of the cylinders 21 extend parallel to that of the cylindrical casing 13. Instead of the provision of four pairs of piston 22 and cylinder 21, it is possible to provide two pairs of piston 22 and cylinder 21 as shown in FIG. 4, or three pairs, or five pairs or more.

Piston 22 is axially slidably and airtightly fitted into cylinder 21, and a tightly enclosed cylinder chamber 23 defined by moving the piston 22 in the direction away from the cylinder 21 is in a vacuum condition. The rear side (the reverse side of the side facing the cylinder chamber 23) of the piston 22 communicates with the atmosphere. Thus, the atmospheric pressure acts to move the piston 22 relative to the cylinder 21 so as to decrease the volume of the cylinder chamber 23.

The piston 22 is formed of a resilient material such as rubber and is fitted as radially compressed into the cylinder 21, so that it closely contacts the inner periphery of the cylinder 21 with no clearance therebetween.

The movable member 14 and four pistons 22 are integrally interconnected by a connection rod 25 bent as substantially U-shaped so that the volume of the cylinder chamber 23 assumes substantially 0 ml when the volume of the load chamber 12 is substantially 0 ml. Thus, the connection rod 25 serves as cooperative means such as to move the movable member 14 and the pistons 22 cooperatively to increase the volume of the load chamber 12 in proportion to an increase in the volume of the cylinder chamber 23 and reduce the volume of the load chamber 12 in proportion to a decrease in the volume of the cylinder chamber 23.

Each cylinder 21 is provided with a communicating port 27 for communication between the cylinder and the atmosphere which is made closable by open-close means 28. The open-close means 28 is a plug formed of a resilient material such as rubber and is removably and airtightly fitted into the communicating port 27 in the form of a circular hole.

A medicinal liquid is infused into a patient body by utilizing the liquid infusion apparatus of the first embodiment in the following manner. The respective volumes of the load chamber 12 and the cylinder chambers 23 are reduced to 0 ml. The spouting port 16 is closed by the open-close valve device 18. The open-close means 28 are fitted into the communicating ports 27. The medicinal liquid is then forcibly injected into the apparatus through the injection port 15 with use of a syringe or the like, thus increasing the volume of the load chamber 12 as well as the volume of the cylinder chambers 23 in a vacuum condition. To inject the medicinal liquid into the apparatus, the connection rod 25 may be lifted by hands or the like relative to the casing 13.

If the projected area of one of the pistons 22 in the moving direction thereof is defined as "Sp", the number of the cylinder chambers 23 in a vacuum condition as "n", the projected area of the movable member 14 in the moving direction thereof as "Sm", the atmospheric pressure as "Pa", and the pressure inside the load chamber 12 as "Pb", then the pressure inside the load chamber 12 relative to the atmospheric pressure "Pa" ("Pa"–"Pb") is worked out from the following equations of condition of equilibrium between the forces exerted on the pistons 22 integrally connected by the connection rod 15 and on the movable member 14:

$$Pa \times nSp + Pa \times Sm = Pb \times Sm \quad Pb - Pa = nPa \times Sp/Sm$$

Consequently, in the load chamber 12 is generated a constant positive pressure which is determined by the values of the projected area "Sp" of the piston 22 in the moving direction thereof, the projected area "Sm" of the movable member 14 in the moving direction thereof, the atmospheric pressure "Pa", and the number "n" of the cylinder chambers 23 in a vacuum condition. The amount of the medicinal liquid in the load chamber 12 does not vary such a positive pressure.

After the tube 20 is confirmed to be surely connected to the spouting port 16 and the patient body, the open-close valve device 18 is operated to open the spouting port 16. Since the constant positive pressure is generated in the load chamber 12 as described above, the medicinal liquid is spouted from the spouting port 16 at a constant flow rate per unit time and infused into the patient body through the tube 20.

As the medicinal liquid is spouted out of the load chamber 12, the movable member 14 and the pistons 22 are integrally moved relative to the casing 13 and the cylinders 21, thereby proportionally reducing the volumes of the load chamber 12 and cylinder chambers 23.

To decrease the flow rate per unit time during such an infusion process of the medicinal liquid into the patient body, the communicating port 27 of any one of the cylinders 21 is opened to make the cylinder chamber 23 thereof communicate with the atmosphere, so that the pressure ("Pa"–"Pb") in the load chamber 12 relative to the atmospheric pressure "Pa" is reduced thereby reducing the flow rate of the medicinal liquid spouted from the spouting port 16. This enables the adjustment of the flow rate of the medicinal liquid.

To supplement the load chamber 12 with medicinal liquid, the spouting port 16 is temporarily closed by operating the open-close valve device 18, and the supplementary liquid is injected from the injection port 15. Thereafter the spouting port 16 is opened by operating the open-close valve device again. This enables continuous infusion of the medicinal liquid in an amount exceeding the maximum capacity of the load chamber 12 into the patient body.

To infuse the medicinal liquid at an extremely small flow rate into the patient body, a flow control device (not shown) which adjusts the flow rate per unit time is generally provided in an intermediate portion of the tube 20. In the conventional balloon infusers, since the spouting pressure of the medicinal liquid spouted from a spouting port is not constant, such a flow control device does not necessarily ensure a constant flow rate. On the other hand, in the liquid infusion apparatus of the subject embodiment of the present invention, since the spouting pressure is inherently constant, the flow rate of the medicinal liquid after passing through the flow control device scarcely varies. Consequently, it is sufficient to adopt an inexpensive device of a simple structure such as a throttle valve as the flow control device which can obtain a required flow rate of the medicinal liquid.

The liquid infusion apparatus 10 according to the first embodiment of the present invention is easy to use and subject to less possibility of failure by virtue of its very simple structure, and is suitable for carrying, particularly suitable for use by a patient receiving regular outpatient treatments by virtue of its light-weight and compact characteristics. Further, the apparatus is readily produced with an extremely reduced cost without any special technique.

As indicated by the two dot chain line in FIG. 1, a hard cover 29 covering connection rod 25 may be removably mounted on the casing 13 or cylinders 21, so that a hand or bed is prevented from inadvertently contacting the connecting rod 25 during the operation of the apparatus 10, thereby ensuring stable operation of the apparatus 10.

(Second Embodiment)

Figure 5:
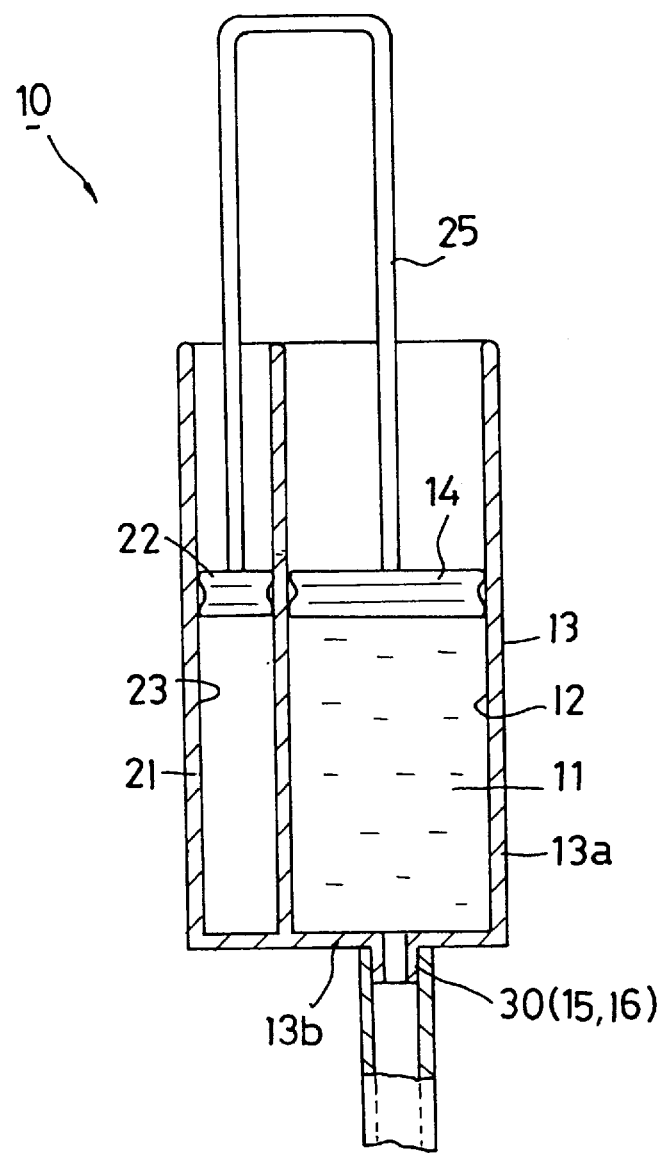
FIG. 5 is a side sectional view of a liquid infusion apparatus according to a second embodiment of the invention.

FIG. 5 shows a second embodiment of the present invention in which the same constituents as those of the aforementioned first embodiment are designated by the same reference numerals as those used in the first embodiment for omission of detailed description thereon. Constituents different from those of the first embodiment and their advantages are to be described.

The second embodiment comprises a pair of cylinder 21 and piston 22, the cylinder 21 not defining a communicating port 27 for communication between cylinder chamber 23 and the atmosphere.

Casing 13 is formed with one injection-spouting port 30 in the bottom wall portion 13b which serves as both injection port 15 for injecting a medicinal liquid into the load chamber 12 and spouting port 16 for spouting the liquid out of the load chamber 12. In use, the medicinal liquid is injected into load chamber 12 through the injection-spouting port 30, and then tube 20 is connected to the injection-spouting port 30.

The tube 20 may be connected to the injection-spouting port 30 either directly or through an open-close valve device (not shown).

The apparatus according to the second embodiment is of highly simplified structure and hence requires further reduced manufacturing cost.

(Third Embodiment)

Figure 6:
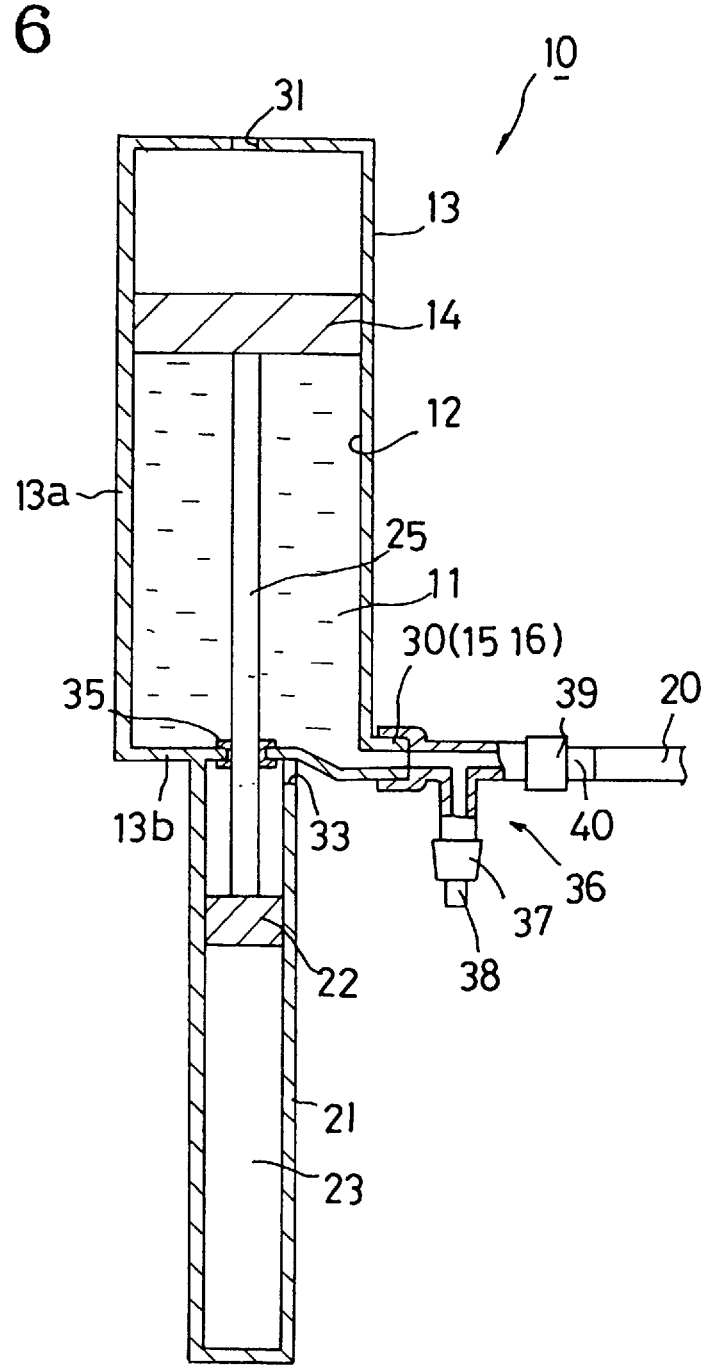
FIG. 6 is a side sectional view of a liquid infusion apparatus according to a third embodiment of the invention.

FIG. 6 shows a third embodiment of the present invention which differs from the aforementioned second embodiment in that casing 13 and cylinder 21 are serially integrally interconnected and that connection rod 25 ( cooperative means) integrally interconnecting movable member 14 and piston 22 is shaped into a straight rod. In this embodiment, the connection rod 25 extends through the casing 13 in the bottom wall portion 13b which is provided with a sealing member 35 on the hole inserted with the rod 25 so as to allow the connection rod 25 to liquid-tightly and airtightly slide. The casing 13 and the cylinder 21 respectively define communication holes 31 and 33 for communication between the respective rear sides of the movable member 14 and piston 22 and the atmosphere.

The injection-spouting port 30 is connected with a bifurcated tube 36 which includes an injection port portion 38 having a one-way valve 37 which allows the injection of the medicinal liquid into load chamber 12 but prevents the flowing out of the liquid therefrom and a spouting port portion 40 having an open-close valve 39.

To charge the load chamber 12 with the medicinal liquid, the medicinal liquid is forcibly injected through the injection port portion 38 using a syringe or the like with the open-close valve 39 closed. When the syringe is removed from the injection port portion 38 after the completion of injection, the one-way valve 37 prevents back-flow and leakage of the injected medicinal liquid.

After tube 20 is confirmed to be surely connected to both the spouting port portion 40 of the bifurcated tube 36 and the patient body, the open-close valve 39 is opened to cause the medicinal liquid 11 in the load chamber 12 to be spouted from the spouting port portion 40 at a constant flow rate.

Other constituents of this embodiment corresponding to those of the second embodiment are respectively designated by the same reference numerals as those used for the corresponding constituents for omission of detailed description thereon.

The third embodiment does not necessarily require the bifurcated tube 36. In the absence of the bifurcated tube 36, the medicinal liquid is injected into the load chamber 12 through the injection-spouting port 30, and then the tube 20 is connected to the injection-spouting port 30, as in the second embodiment.

(Fourth Embodiment)

Figure 7:
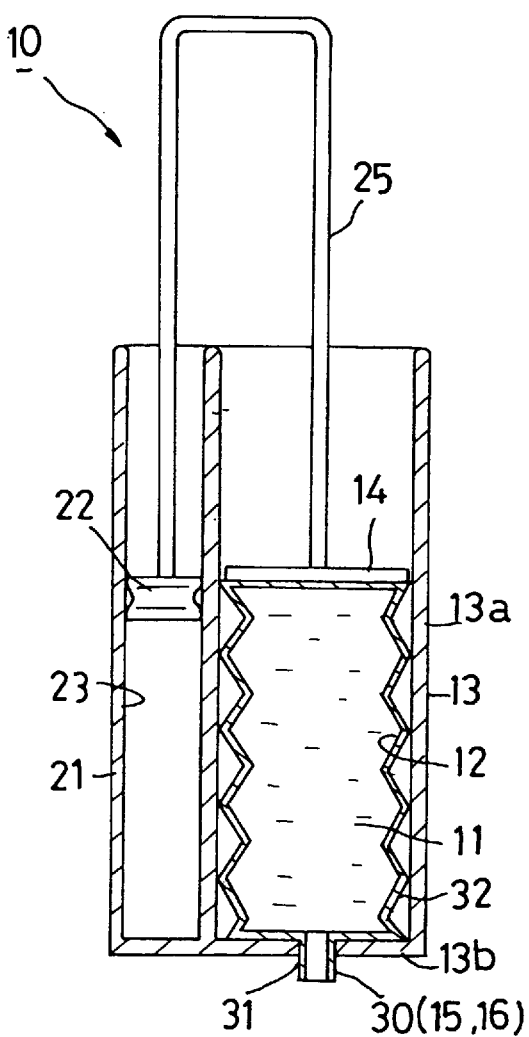
FIG. 7 is a side sectional view of a liquid infusion apparatus according to a fourth embodiment of the invention.

FIG. 7 shows a fourth embodiment of the present invention in which constituents corresponding to the constituents of the aforementioned second embodiment are respectively designated by the same reference numerals as those used for the corresponding constituents for omission of detailed description thereon. Other constituents different from those of the second embodiment and their advantages are to be described.

In this embodiment, casing 13 accommodates therein a retractable container 32 in the form of bellows made of a soft synthetic resin. Load chamber 12 for loading a medicinal liquid comprises an inner space of the retractable container 32 which is expansible and retractable axially of the peripheral wall portion 13a of the casing 13 so as to increase and decrease the volume of the load chamber 12. The form of the retractable container 32 is not limited to the bellows and may be, for example, a bag.

The retractable container 32 has one end in its expanding-retracting direction which is fixed to the bottom wall portion 13b of the casing 13 and the other end which is fixed to movable member 14 in the form of a disc. The movable member 14 is formed of a hard material (for example, metal or hard synthetic resin or the like) and is adapted to be guided by the inner periphery of the peripheral wall portion 13a of the casing 13 so as to be movable axially of the casing 13.

At aforesaid one end of the retractable container 32 in its expanding-retracting direction is formed an injection-spouting port 30 which extends through the communication hole 31 defined in the bottom wall portion 13b of the casing 13 and protrudes outward from the casing 13.

The fourth embodiment ensures the same functions and advantages as the above-mentioned second embodiment. The second embodiment requires precision in manufacturing the casing and the movable member for the airtight slide of the movable member along the peripheral wall portion of the casing. On the other hand, the fourth embodiment does not require such precision, and in addition the retractable container 32 can be readily integrally molded at a reduced cost by, for example, blow molding. Furthermore, the apparatus according to this embodiment is free of slide friction between the casing 13 and the movable member 14 and hence provides a reduced operational resistance.

The casing 13 of the fourth embodiment is not necessarily of a cylindrical configuration. It is only required that the casing 13 be formed so as to fix the retractable container 32 at its one end in the expanding-retracting direction thereof. For example, the casing 13 may be formed as having only the bottom wall portion 13b without the peripheral wall portion 13a.

Further, an arrangement may be adopted such that the retractable container 32 is removably mounted in the space between the casing 13 and the movable member 14 while an opening is defined in the peripheral wall portion 13a of the casing 13 to allow the retractable container 32 to removably fit into the casing 13, whereby the retractable container 32 serves as a replaceable container. In such an arrangement, the retractable container 32 is preferably fixed to the casing 13 and the movable member 14 with a double-coated adhesive tape or the like.

The retractable container 32 is not necessarily fixed to the casing 13 or the movable member 14 and may only be fitted into the space between the casing 13 and the movable member 14. Even in such an arrangement, the medicinal liquid can be filled into the load chamber 12 by forcibly injecting the liquid through the injection-spouting port 30 of the retractable container 32, and the container 32 held between the casing 13 and the movable member 14 is prevented from falling off.

(Fifth Embodiment)

Figure 8:
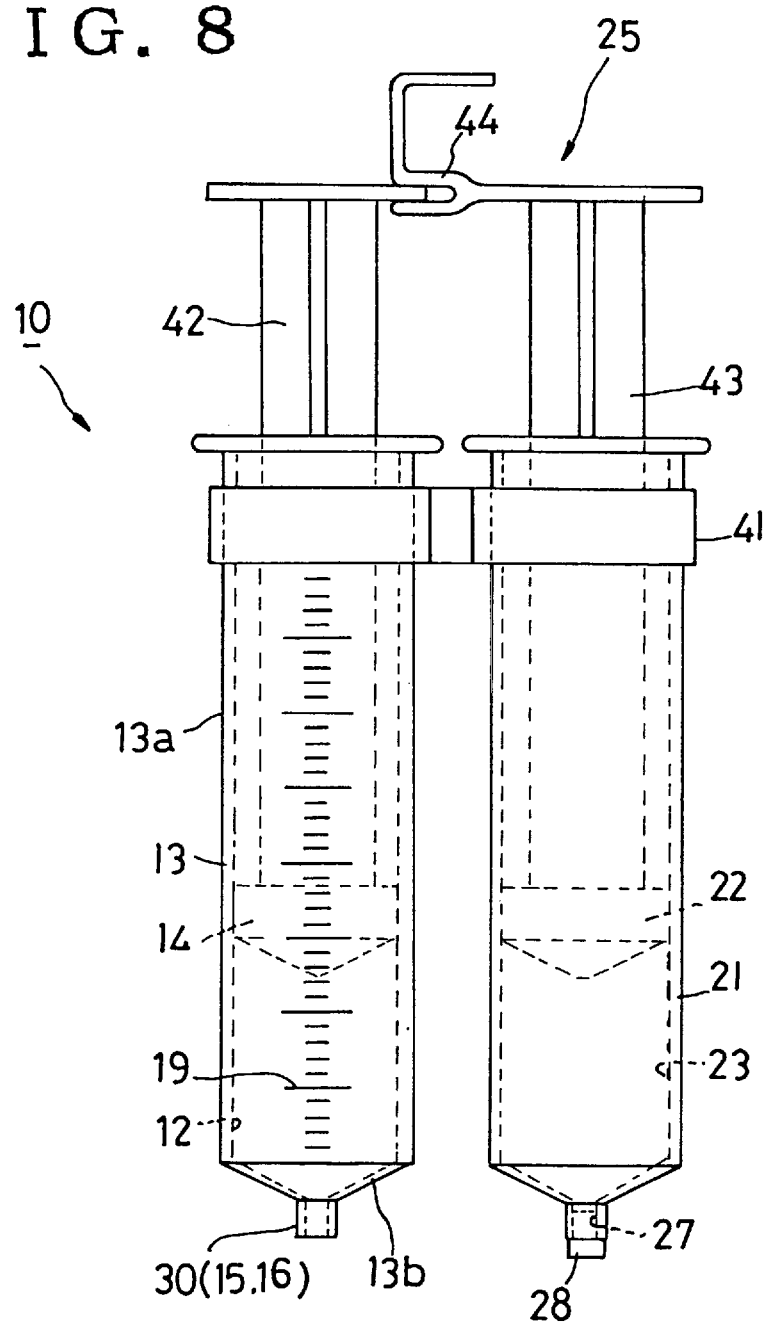
FIG. 8 is a side sectional view of a liquid infusion apparatus according to a fifth embodiment of the invention.

FIG. 8 shows a fifth embodiment of the present invention in which constituents corresponding to the constituents of the aforementioned second embodiment are respectively designated by the same reference numerals as those used for the corresponding constituents for omission of detailed description thereon. Other constituents different from those of the second embodiment and their advantages are to be described.

A liquid infusion apparatus 10 according to the fifth embodiment of the present invention comprises a casing 13 and a cylinder 21 which are separately formed and separably and integrally connected to each other by a coupling member 41. The coupling member 41 fits around both the casing 13 and the cylinder 21, so that the casing 13 and the cylinder 21 are restrained from relative movement in the axial direction.

To movable member 14 is integrally coupled a first plunger 42 projecting axially outwardly from an open end of the casing 13, while to piston 22 is integrally coupled a second plunger 43 projecting axially outwardly from an open end of the cylinder 21.

The flange at the upper end of the second plunger 43 has an engagement portion 44 which disengageably engages the first plunger 42 of the movable member 14. The plungers 42 and 43 are integrally interconnected by making the engagement portion 44 engage the upper end flange of the first plunger 42. Therefore, the plungers 42 and 43 constitute a cooperative means 25 which is inactivated when the engagement portion 44 is disengaged from the first plunger 42.

The second plunger 43 may be formed without the engagement portion 44, and the plungers 42 and 43 may be integrally coupled to each other with, for example, a coupling attachment (not shown) which is detachably attached to both the plungers 42 and 43.

According to the fifth embodiment, since the casing 13 and cylinder 21 can be manufactured separately, they enjoy their simplified structures and hence can be readily manufactured using molds which can also be readily manufactured, thus resulting in a further reduction in manufacturing cost.

In use of the liquid infusion apparatus 10 of this embodiment, for example, a plurality of casings 13 having respective load chambers preloaded with medicinal liquid may be prepared to be attached to and detached from the cylinder 21 one by one for replacement, so that the medicinal liquid can be continuously infused into a patient body.

Further, it is possible to use commercially available syringes as the casing 13 and cylinder 21.

(Sixth Embodiment)

Figure 9:
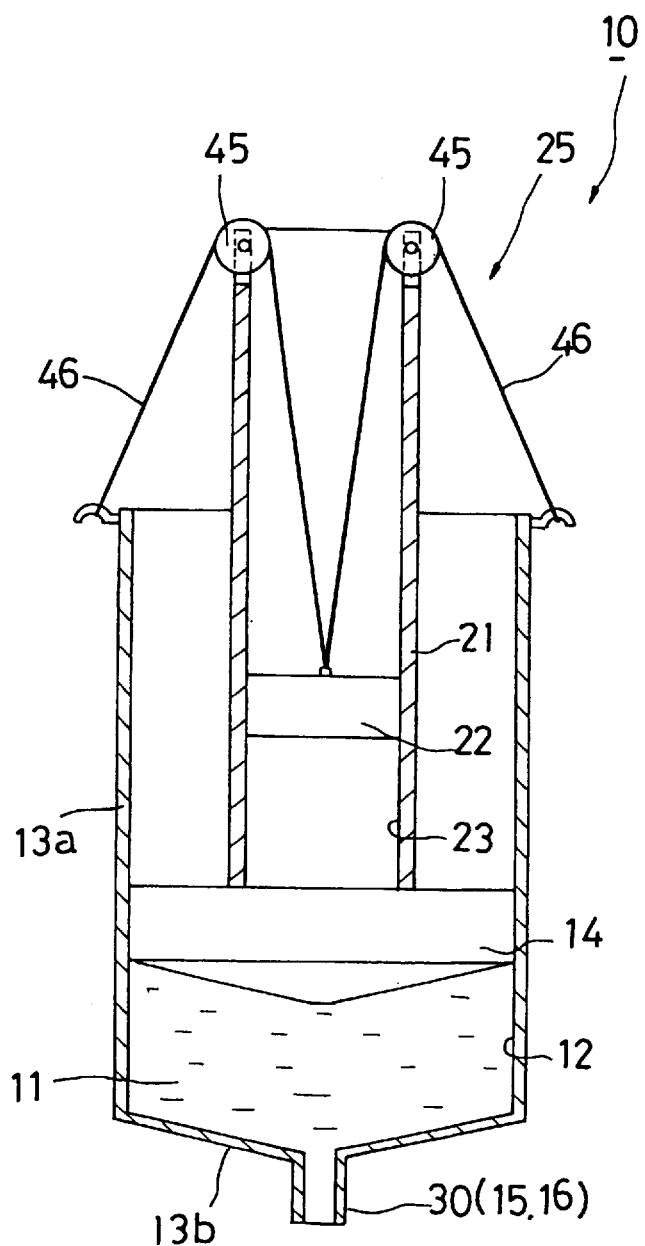
FIG. 9 is a side sectional view of a liquid infusion apparatus according to a sixth embodiment of the invention.

FIG. 9 shows a sixth embodiment of the present invention in which constituents corresponding to the constituents of the aforementioned second embodiment are respectively designated by the same reference numerals as those used for the corresponding constituents for omission of detailed description thereon. Other constituents different from those of the second embodiment and their advantages are to be described.

In a liquid infusion apparatus 10 of this embodiment, cylinder 21 is integrally coupled to the rear side of movable member 14 in coaxial relation to the peripheral wall portion 13a of casing 13.

To piston 22 is connected one end of a flexible linear member 46, such as a thread and a wire, the other end thereof being connected to the peripheral wall portion 13a of the casing 13. An intermediate portion of the linear member 46 passes around a pulley 45 provided on the open end of the cylinder 21 so as to double the force pressing the piston 22 toward the cylinder chamber 23 due to the atmospheric pressure and transmit it to the cylinder 21. Thus, the linear member 46 serves as cooperative means 25. Although it is preferred that two such liner members 46 be used as shown in FIG. 9, one or more than two liner members may be used.

In the sixth embodiment, the cylinder 21 is located inside the peripheral wall portion 13a of the casing 13 and, hence the liquid infusion apparatus 10, as a whole, enjoys a compact construction.

(Seventh Embodiment)

Figure 10:
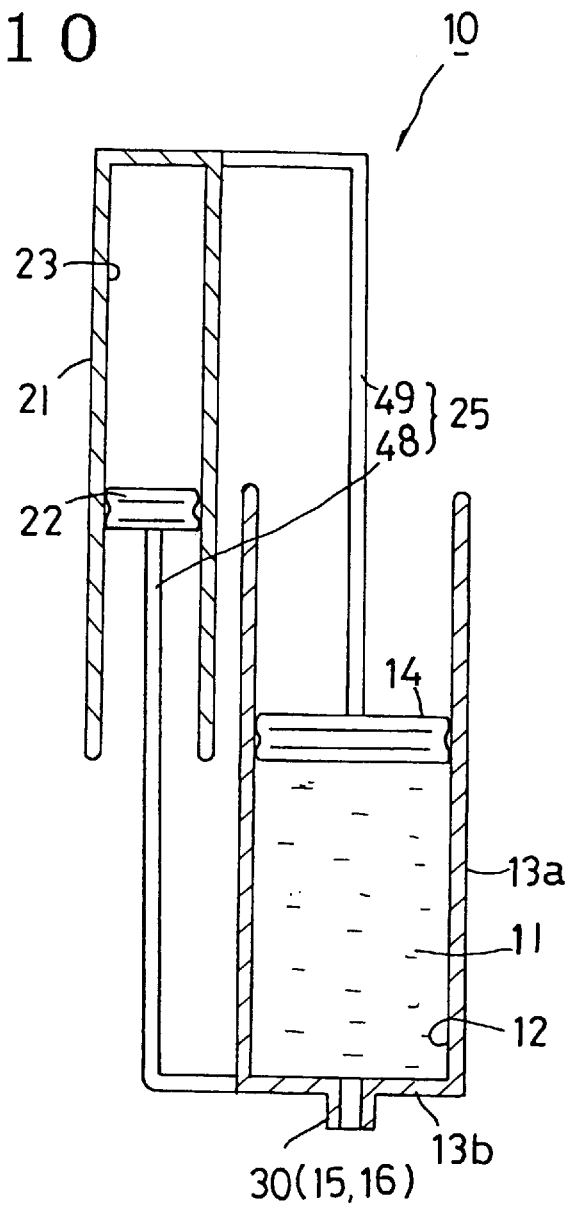
FIG. 10 is a side sectional view of a liquid infusion apparatus according to a seventh embodiment of the invention.

FIG. 10 shows a seventh embodiment of the present invention in which constituents corresponding to the constituents of the aforementioned second embodiment are respectively designated by the same reference numerals as those used for the corresponding constituents for omission of detailed description thereon. Other constituents different from those of the second embodiment and their advantages are to be described.

A liquid infusion apparatus 10 according to the seventh embodiment of the present invention comprises a casing 13 and a cylinder 21 which are separately formed and disposed as having respective axes extending parallel to each other and respective open ends oriented in opposite directions.

The casing 13 and piston 22 are integrally coupled to each other with a substantially L-shaped connection rod 48, and the cylinder 21 and movable member 14 are integrally coupled to each other with a substantially L-shaped connection rod 49. Thus, the connection rods 48 and 49 serve as cooperative means 25.

(Eighth Embodiment)

FIGS. 11 to 14 show the eighth embodiment of the present invention which is the best mode of the vertical type apparatus having a casing 13 and a cylinder 21 coaxially and vertically connected in series.

Figure 11:
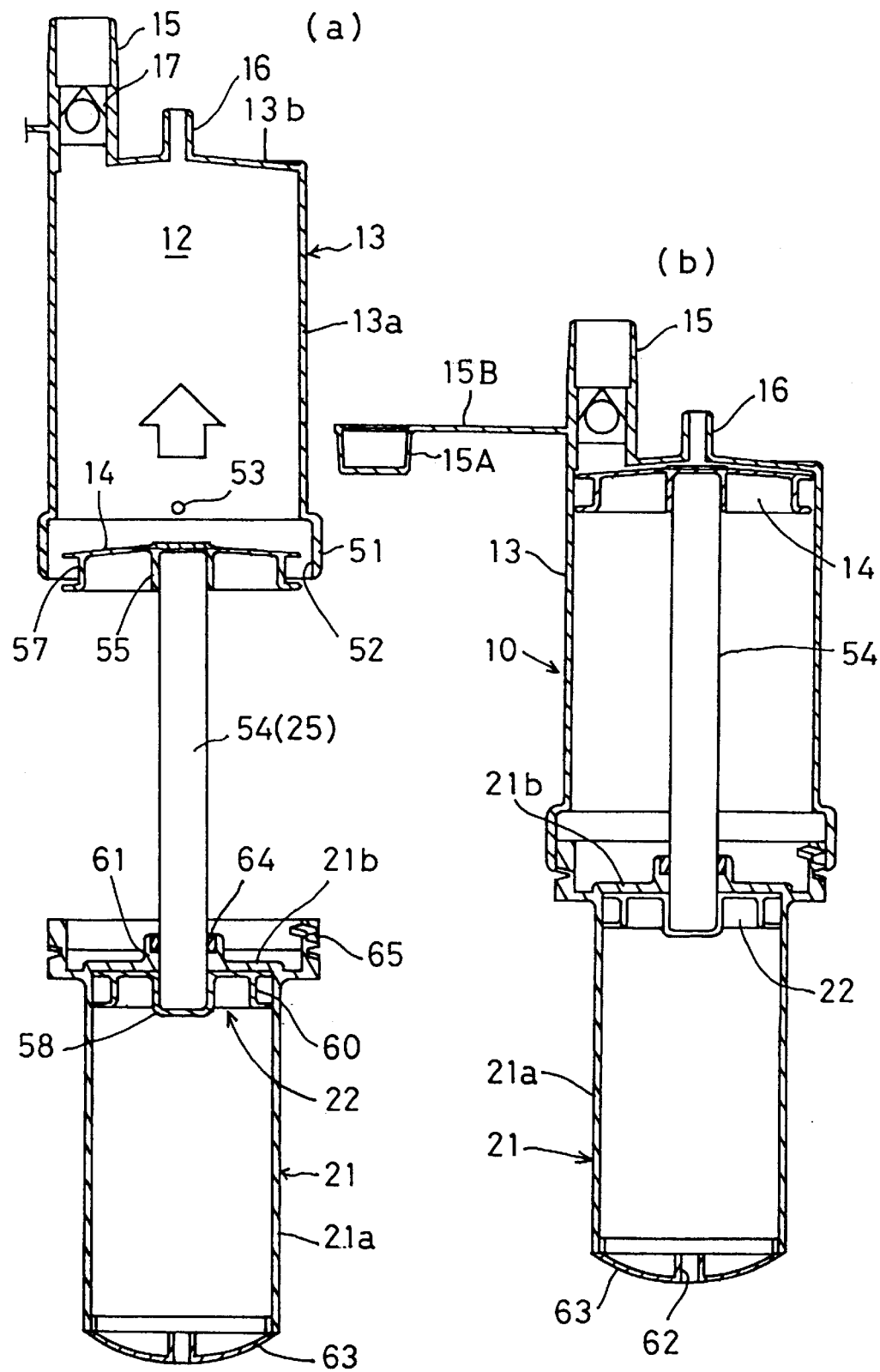
FIG. 11 is a side sectional view of a liquid infusion apparatus according to a eighth embodiment of the invention, including FIG. 11(a) showing the state thereof prior to the mounting of the cylinder and FIG. 11(b) showing the state thereof after the mounting of the cylinder.

The casing 13 used in a liquid infusion apparatus 10 according to this embodiment is of a cylindrical configuration having one end closed by a bottom wall portion 13b (upper end of the casing 13 in the FIG. 11) and the other end opened (lower end of the casing 13 in the FIG. 11). The bottom wall portion 13b of the casing 13 is formed with an injection port 15 and a spouting port 16.

The injection port 15 projects from an edge portion of the bottom wall portion 13b and has a non-return valve (a valve device) 17 therein, while the spouting port 16 projects outwardly of a central portion of the bottom wall portion 13b in the axial direction of the casing 13 and is connected to a tube 20 having an open-close valve 18.

To the peripheral wall of the injection port 15 is integrally secured a cap 15A through a coupling wire 15B for detachably capping the end portion of the injection port 15. This embodiment may have only one injection-spouting port 30 as in the aforementioned second embodiment shown in FIG. 5 for simplifying the structure thereof.

If, of the casing 13 and cylinder 21, at least the casing 13 is formed of a transparent or translucent synthetic resin, the provision of graduations on the casing 13 enables accurate measurement of the medicinal liquid 11 in the load chamber 12.

The open end of the peripheral wall portion 13a of the casing 13 has a larger diameter portion 51 internally formed with a female screw portion 52, the larger diameter portion 51 being slightly larger in diameter than the rest. A small hole 53 for communication between the inside of the casing 13 and the atmosphere is defined adjacent the larger diameter portion 52.

The small hole 53 permits the space on the rear side of movable member 14 in the casing 13 (below the movable member 14 in FIG. 11) to communicate with the atmosphere so as to allow an axial movement of the movable member 14. The small hole 53 is closed by a filter 53A which allows the air to pass therethrough but restrains bacteria from penetration. Accordingly, even when the infusion apparatus 10 is continuously used in such a way that medicinal liquid 11 is infused into a patient body while supplementary medicinal liquid is injected into the load chamber through the injection port 15, the filter 53A prevents the penetration of bacteria into the medicinal liquid 11 and hence keeps the human body from infection.

Figures 12, 12A, 12B:
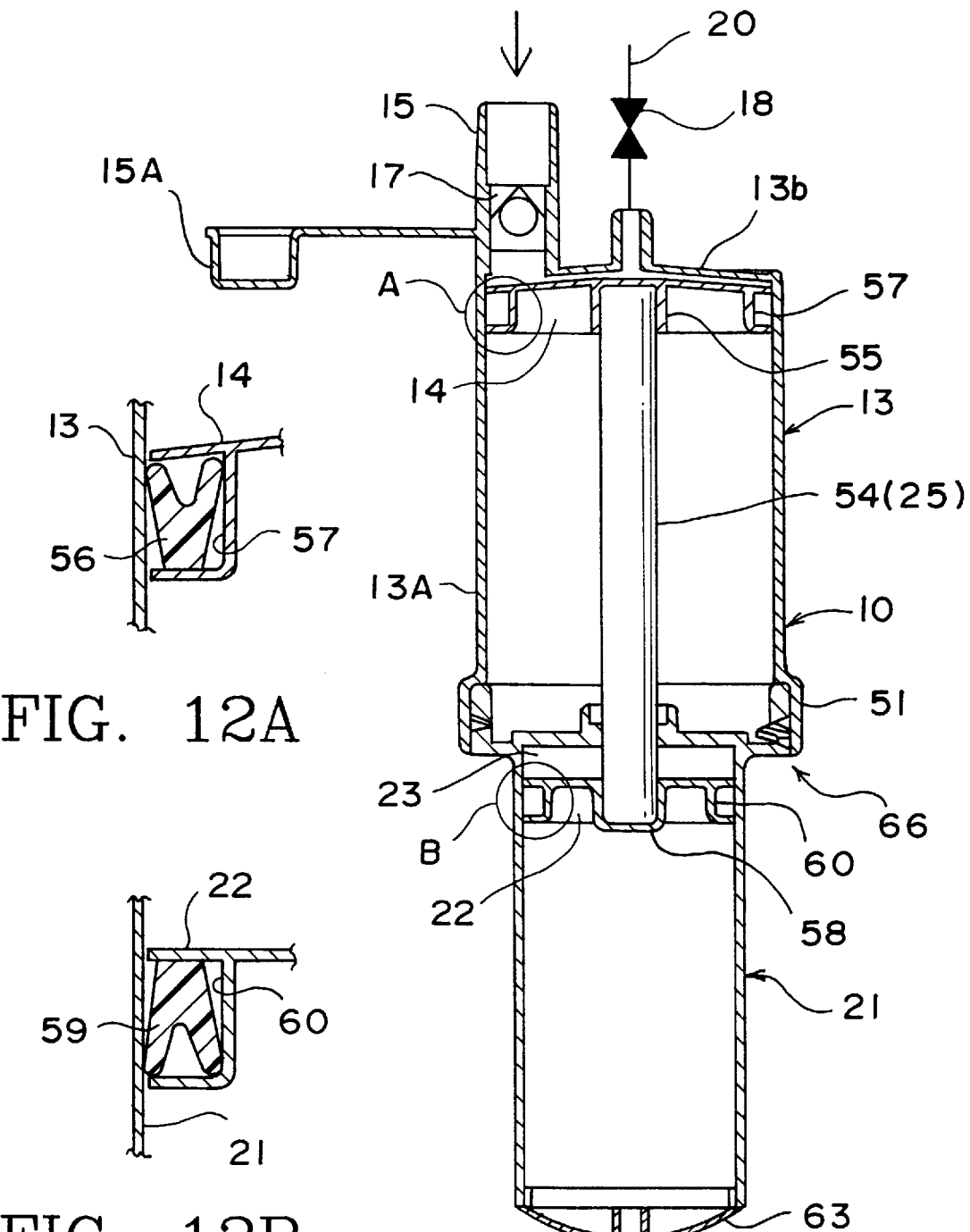
FIG. 12 is a side sectional view of the liquid infusion apparatus according to the eighth embodiment in the state where screw-in is completed.

In this embodiment, the movable member 14 is liquid-tightly and axially movably fitted into the casing 13 so that the load chamber 12 for storing the medicinal liquid 11 is defined on one side (upper side in FIG. 11) within the casing 13. As shown in FIG. 12, the movable member 14 is shaped into a disc having a tapered surface slightly bulged in a central portion thereof, like the bottom wall portion 13b of the casing 13. The movable member 14 has a fitting portion 55 in a central portion of the reverse side thereof for securing a connection rod 54, and a peripheral groove 57 in the peripheral edge thereof for receiving a seal ring 56.

The connection rod 54, which functions as cooperative means 25, is a linear rod extending axially of the casing 13 toward the aforesaid other end thereof which is fitted into the fitting portion 55 at one end thereof, thereby being secured to the central portion of the movable member 14. The other end of the connection rod 54 is secured to a central portion of piston 22. Thus, the piston 22 is cooperatively connected to the movable member 14 in coaxial relation to each other. The piston 22 is shaped into a disc having a fitting portion 58 in a central portion of the reverse side thereof for securing the connection rod 54 and a peripheral groove 60 in the peripheral edge thereof for receiving a seal ring 59.

The seal rings 56 and 59 each comprise a rubber packing substantially V-shaped in section. By positioning the seal ring 56 in the peripheral groove 57 of the movable member 14 so that the pressing surface thereof (the surface on the side where the V-shaped section is opened) is oriented toward the load chamber 12 as shown in FIG. 12, the medicinal liquid 11 is assuredly prevented from leaking from the load chamber 12. The seal ring 59 is positioned in the peripheral groove 60 of the piston 22 so that the pressing surface thereof is oriented toward the aforementioned other end of the cylinder 21 (toward the side receiving the atmospheric pressure). This enables the vacuum cylinder chamber 23 to surely prevent entrance of air thereinto.

The cylinder 21 of this embodiment comprises a cylindrical peripheral wall 21a having one end closed integrally by a bottom portion 21b centrally provided with a boss portion 61 and the other end opened and fixedly attached with a domed lid member 63 centrally defining a vent hole 62.

The boss portion 61 of the bottom portion 21b is provided with a rubber seal ring 64 and the connection rod 54 is inserted through the boss portion 61, thereby airtightly closing one internal end of the cylinder 21. The seal ring 64 in the boss portion 61 comprises a packing substantially V-shaped in section like the seal rings 56 and 59 and is positioned so that the pressing surface thereof is oriented toward the casing 13 (upwardly in FIG. 12). Since the vent hole 62 is provided in the lid member 63, the other end side of the piston 22 communicates with the atmosphere.

Thus, the connection rod 54 is airtightly inserted through the bottom portion 21b of the cylinder 21 with the other end of the cylinder 21 communicating with the atmosphere, while the piston 22 is airtightly and axially movably inserted into the cylinder 21.

A male screw portion 65 protrudes from the aforesaid one end of the cylinder 21. By screwing this male screw portion 65 into the female portion 52 formed at the aforesaid opened other end of the casing 13, it is possible to coaxially connect the cylinder 21 to the casing 13. Accordingly, the male and female portions 65 and 52 constitute connection means 66 interconnecting the cylinder 21 and the casing 13.

As shown in FIG. 11(b), the connection rod 54 is made to have a length slightly longer than the axial length of the casing 13 so as to protrude axially outwardly (downwardly in FIG. 11) from the aforesaid other end of the casing 13 when the movable member 14 abuts the bottom wall portion 13b of the casing 13.

Thus, when the male screw portion 65 of the cylinder 21 is screwed into the female screw portion 52 of the casing 13 with the movable member 14 within the casing 13 being located closest to the aforesaid one end of the casing 13, the cylinder chamber 23 in a vacuum condition is already defined between the bottom portion 21b of the cylinder 21 and the piston 22.

The operation of the liquid infusion apparatus 10 according the eighth embodiment is as follows.

First, as shown in FIG. 11(a), the movable member 14 is inserted into the casing 13 from the opened other end to the bottom wall portion 13b with the spouting port 16 being opened. Subsequently, as shown in FIG. 11(b), the male screw portion 65 of the cylinder 21 is fitted into the female screw portion 52 of the casing 13 and the cylinder 21 is rotated relative to the casing 13 about the axis thereof in the screw-in direction, so that the cylinder 21 is screwed in and connected to the aforesaid other end of the casing 13.

Since the connection rod 54 is slightly longer than the casing 13, the piston 22 is spaced apart from the bottom portion 21b of the cylinder 21 upon completion of the screwing-in of the cylinder 21 against the casing 13, as shown in FIG. 12. This allows flat and vacuum cylinder chamber 23 defined between the bottom portion 21b and the piston 22 to be formed within the cylinder 21 on the one end side thereof.

Figure 13:
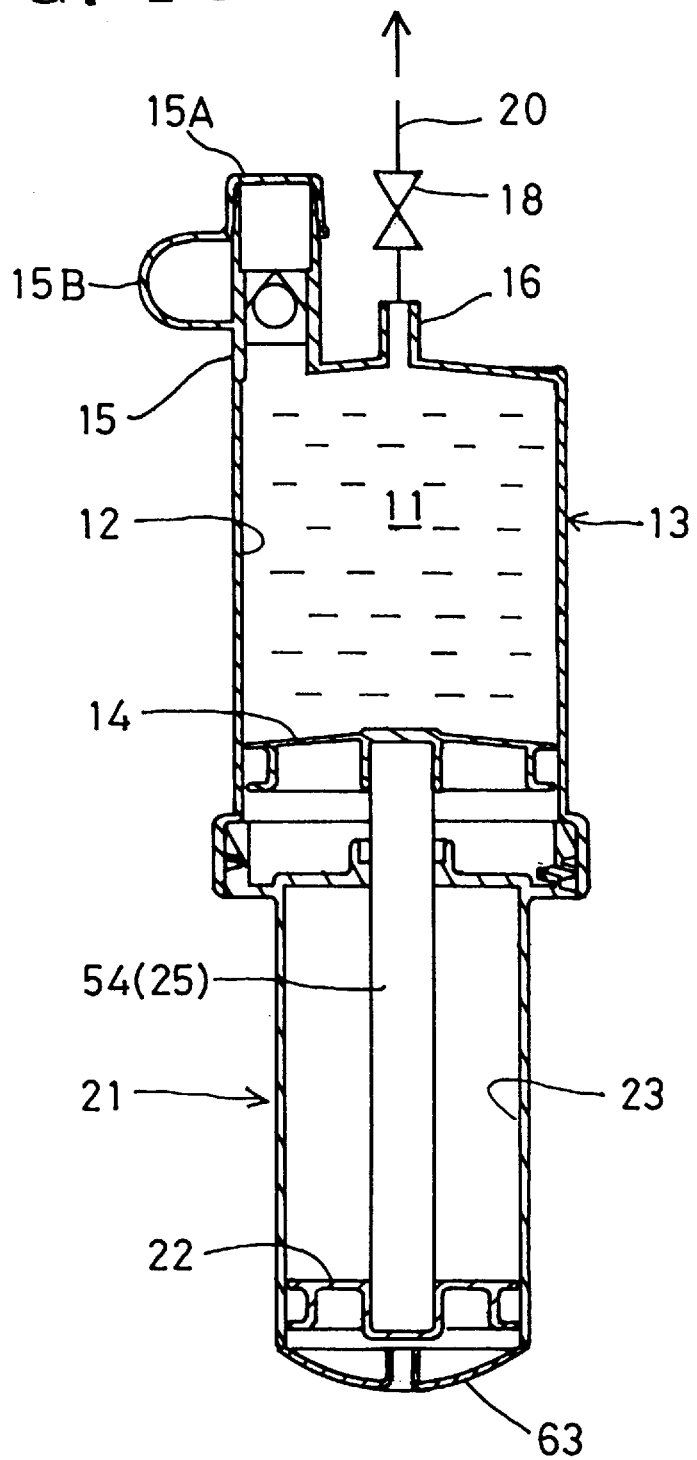
FIG. 13 is a side sectional view of the liquid infusion apparatus according to the eighth embodiment in the state where infusion is initiated.
Figure 14:
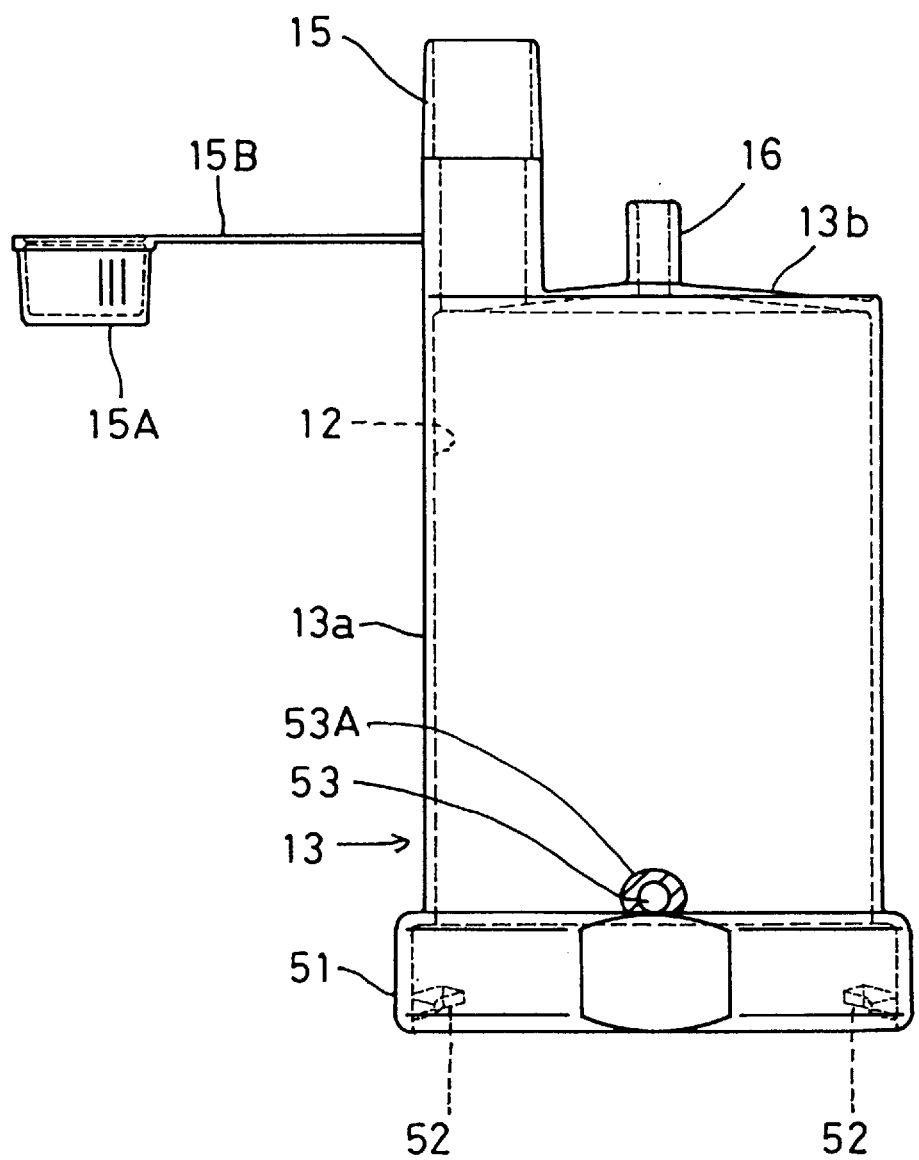
FIG. 14 is a side elevational view of the casing of the liquid infusion apparatus according to the eighth embodiment.

Thereafter, the open-close valve 18 of the spouting port 16 is closed and medicinal liquid 11 is forcibly injected into the apparatus through the injection port 15 with use of a syringe or the like. With the injection of the medicinal liquid 11, the movable member 14 moves toward the aforesaid other end of the casing 13 (downwardly) thereby increasing the volume of the load chamber 12 defined in front of the movable member 14. At the same time therewith, the piston 22 moves toward the aforesaid other end of the cylinder 21 thereby gradually increasing the volume of vacuum cylinder chamber 23. When the piston 22 reaches a location adjacent the lid member 63 as shown in FIG. 13, preparation for infusion is completed.

In turn, when the injection port 15 is capped with the cap 15A and the open-close valve 18 of the spouting port 16 is closed, the medicinal liquid 11 is infused into a patient body through the tube 20 connected to the spouting port 16.

In the liquid infusion apparatus 10 according to this embodiment, since vacuum cylinder chamber 23 is already formed prior to the injection of the medicinal liquid 11 into the casing 13, the movable member 14 is pressed by a constant negative pressure up to the last extremity at which the volume of the load chamber 12 assumes zero. This enables the medicinal liquid 11 in the casing 13 to be almost completely spouted from the apparatus, thus avoiding wasteful use of the medicinal liquid 11.

Further, since the connection means 66 of the screw-in type connects the cylinder 21 to the opened other end of the casing 13, it is possible to remove the casing 13 from the cylinder 21 with ease after the completion of the infusion of the medicinal liquid 11 into the patient body. Hence, the apparatus 10, though it is of the vertical type in which the casing 13 and the cylinder 21 are serially interconnected, enjoys an advantage that the inside of the casing 13 can readily be cleaned or sterilized.

It should be noted that if the apparatus 10 of this embodiment is adapted to be hung from the neck of a patient or the like so that the bottom wall portion 13b of the casing 13 provided with both the injection port 15 and the spouting port 16 is oriented upward, the apparatus 10 offers excellent portability with the tube 20 shortened as much as possible.

While the embodiments of the present invention have been described in detail, such embodiments are not limitative of the present invention and can be modified in design.

In other words, the present invention can be carried out in other manners without departing from the essential features of the invention. The embodiments described in this specification are only illustrative and non-limitative of the present invention. The scope of the present invention is defined by the following claims and covers all variations derived from the claims.

INDUSTRIAL APPLICABILITY

The present invention relates to a liquid infusion apparatus which is useful, in particular, for infusing a medicinal liquid into a human or animal body.

What is claimed is:

1. A liquid infusion apparatus comprising:
   a casing (13) defining therein a load chamber (12) to be loaded with a liquid and having a liquid injection port (15) and a spouting port (16) which communicate with the load chamber (12);
   a movable member (14) forming part of a wall of the load chamber (12) and liquid-tightly and axially movably fitted into the casing (13) so as to vary the volume of the load chamber (12);
   a cylinder (21) coaxially connected to one axial end of the casing (13) and capable of forming a vacuum chamber (23) therein;

a piston (22) forming part of a wall of the vacuum chamber (23) and axially movably and airtightly inserted into the cylinder (21) for varying the volume of the vacuum chamber (23);

an intermediate wall (13b)(21b) disposed in a portion connecting the casing (12) and the cylinder (21) to separate respective internal spaces of the casing (12) and cylinder (21) from each other;

a connection rod (25) having an axially intermediate portion airtightly extending through the intermediate wall (13b)(21b), one end connected to the movable member (14) and an opposite end connected to the piston (22); and a first air hole (31)(53) formed in a wall portion of the casing (13) and cylinder (21) which does not define the load chamber (12), and a second air hole (33)(62) formed in a wall portion of the casing (13) and cylinder (21) which does not define the vacuum chamber (23).

2. The liquid infusion apparatus according to claim 1, wherein the first air hole (53) is covered with a filter (53A) which allows communication of air while preventing penetration of bacteria into the apparatus.

3. The liquid infusion apparatus according to claim 1, wherein the connection rod (25) is made to have a length such that when the volume of the load chamber (12) becomes zero due to movement of the movable member (14), the piston (22) remains positioned to form the vacuum chamber (23).

4. The liquid infusion apparatus according to claim 1, wherein a single injection-spouting port (30) serves as both the injection port (15) and the spouting port (16).

5. The liquid infusion apparatus according to claim 1, wherein the injection port (15) and the spouting port (16) are provided separately, and the injection port (15) is provided with a valve device (17) for preventing the liquid in the load chamber (12) from flowing out of the injection port (15).

6. A liquid infusion apparatus comprising:

a casing (13) having a load chamber (12) to be loaded with a liquid;

a movable member (14) forming part of a wall of the load chamber (12) and adapted to reciprocate with respect to the casing (13) to vary the volume of the load chamber (12);

a cylinder (21) integrally coupled to the casing (13);

a piston (22) axially slidably and airtightly fitted in the cylinder (21);

the casing (13) being formed with an injection port (15) and a spouting port (16) which communicate with the load chamber (12);

the cylinder (21) and the piston (22) defining an airtight cylinder chamber (23) in a vacuum condition when the piston (22) is moved in the direction away from the cylinder (21);

the movable member (14) and the piston (22) being cooperatively interconnected through a cooperative means (25) so as to decrease the volume of the load chamber (12) in proportion to a decrease in the volume of the cylinder chamber (23); and the pair of the cylinder (21) and the piston (22) comprising plural pairs of cylinder (21) and piston (22), at least one of the cylinders (21) defining a communicating port (27) through which the corresponding cylinder chamber (23) communicates with the atmosphere and which is closable by way of an open-close means (28).

7. The liquid infusion apparatus according to claim 6, wherein a single injection-spouting port (30) serves as both the injection port (15) and the spouting port (16).

8. The liquid infusion apparatus according to claim 6, wherein the injection port (15) and the spouting port (16) are provided separately, and the injection port (15) is provided with a valve device (17) for preventing the liquid in the load chamber (12) from flowing out of the injection port (15).

9. The liquid infusion apparatus according to claim 6, wherein the plural cylinders (21) are fixed on the outer periphery of one casing (13) circumferentially equidistantly with their axes parallel to the axis of the casing (13).

10. A liquid infusion apparatus comprising: a casing (13) shaped cylindrical and including a bottom wall portion (13b) which is formed with a liquid injection port (15) and is closing one end of the casing (13) with the other end opened, and a peripheral wall (13a) defining a small hole for communication between the inside of the casing (13) and the atmosphere; a movable member (14) liquid-tightly and axially movably inserted into the casing (13) so as to define within the casing (13) and adjacent the one end thereof a load chamber (12) for storing a liquid from the injection port (15); a piston (22) coaxially and cooperatively connected to the movable member (14) through a connection rod (54) extending toward the other end of the casing (13); a cylinder (21) having one end closed by a bottom portion (21b) into which the connection rod (54) is airtightly inserted and the other end communicating with the atmosphere, the cylinder (21) being airtightly and axially movably fitted around the piston (22); and a connection means (66) for coaxially connecting the cylinder (21) to the casing (13) by screwing the one end of the cylinder (21) into the opened other end of the casing (13).

11. The liquid infusion apparatus according to claim 10, wherein the connection rod (54) is made to have a length such that when the one end of the cylinder (21) is screwed into the opened other end of the casing (13) with the movable member (14) within the casing (13) being located closest to the one end of the casing (13), a vacuum cylinder chamber (23) is already defined between the bottom portion (21b) of the cylinder (21) and the piston (22) within the cylinder (21).

12. The liquid infusion apparatus according to claim 11, wherein the small hole (53) of the peripheral wall (13a) of the casing (13) which is situated on the side where the other end of the casing (13) exists is covered with a filter (53A) preventing penetration of bacteria into the casing (13).

13. The liquid infusion apparatus according to claim 12, wherein the bottom wall portion (13b) of the casing (13) having the injection port (15) is formed with a liquid spouting port (16); and the injection port (15) is provided with a non-return valve (17) for preventing the liquid in the load chamber (12) from flowing back to the exterior of the apparatus.

14. The liquid infusion apparatus according to claim 12, wherein the injection port (15) is an injection-spouting port (30) for serving also as a spouting port (16).

15. The liquid infusion apparatus according to claim 10, wherein of the casing (13) and the cylinder (21) at least the casing (13) is formed of a transparent or translucent synthetic resin.

16. The liquid infusion apparatus according to claim 10, wherein the movable member (14) is provided with a seal ring (56) on the periphery thereof, the seal ring (56) comprising a packing which is substantially V-shaped in section and is positioned so that a pressing surface thereof is oriented toward the load chamber (12); and the piston (22) is provided with a seal ring (59) on the periphery thereof, the seal ring (59) comprising a packing which is substantially V-shaped and is positioned so that a pressing surface thereof is oriented toward the other end of the cylinder (21).

* * * * *